United States Patent [19]

Intemann et al.

[11] Patent Number: 5,526,122
[45] Date of Patent: Jun. 11, 1996

[54] METHOD FOR DETERMINING THE MASS FLOW OF GASES ON THE BASIS OF OPTICAL ABSORPTION AND EMPLOYMENT OF SAID METHOD

[75] Inventors: Andreas Intemann, Munich; Heinrich Körner, Bruckmühl; Konrad Hieber, Grasbrunn, all of Germany

[73] Assignee: Siemens Aktiengesellschaft, Munich, Germany

[21] Appl. No.: 137,079

[22] PCT Filed: Feb. 27, 1992

[86] PCT No.: PCT/DE92/00157

§ 371 Date: Mar. 14, 1994

§ 102(e) Date: Mar. 14, 1994

[87] PCT Pub. No.: WO93/17304

PCT Pub. Date: Sep. 2, 1993

[51] Int. Cl.⁶ .................................................. G01N 21/85
[52] U.S. Cl. .......................... 356/411; 250/356.1; 356/72
[58] Field of Search ................................. 356/410, 411, 356/435, 437, 72, 73; 250/345, 356.1

[56] References Cited

U.S. PATENT DOCUMENTS 3,654,109  4/1972  Hohl et al. ...................... 250/356.1 X

FOREIGN PATENT DOCUMENTS 0215287  3/1987  Germany.
4032962  4/1992  Germany.

OTHER PUBLICATIONS

Patent Abstract of Japan, vol. 15, No. 133 (C-820) 2 Apr. 1991; JP A 30 16 555, NEC, Jan. 1991.
"Second Generation-Analyzer Cross Flow Modulation/ Techniques Precision, Sensitive, Continuous Measurements", Adv. in Instrumentation, 42 (1987) Part 1, pp. 547-555, Research Triangle Park, NC, USA.
Company brochure, "Vaporizer Controllers et al.", Apr. 1987, pp. 5-9, 20 by Tylan GmbH, Eching/Munich, Germany.
Company brochure, "GASANALYSEGERATE ULTRAMAT 5 . OXYMAT 5", Siemens AG, Germany No. A19100-E681-A21-V4. No month & date available.
Company brochure, "V-Max The Ultimate Vapor Source", by Tylan GmbH, Eching/Munich, Germany. No month & date available.

Primary Examiner—Vincent P. McGraw
Attorney, Agent, or Firm—Hill, Steadman & Simpson

[57] ABSTRACT

In the method, the totality of the gases is conducted through an absorption cell. A reference cell contains a reference gas. The cells are optically transirradiated and a signal representing a quantity for the mass flow to be identified is generated in a detector which picks up the optical radiation emerging from the cells.

15 Claims, 1 Drawing Sheet

METHOD FOR DETERMINING THE MASS FLOW OF GASES ON THE BASIS OF OPTICAL ABSORPTION AND EMPLOYMENT OF SAID METHOD

BACKGROUND OF THE INVENTION

1. Field of the Invention

The present invention is directed to a method for determining the mass flow of gases on the basis of optical absorption.

2. Description of the Related Art

Fluid and solid initial materials or substances that have a low vapor pressure and a low vapor pressure in comparison to previously standard gases such as, for example, $SiH_4$, $B_2H_6$ are being increasingly employed in CVD coating processes (chemical vapor deposition) in many areas of technology, for example in microelectronics or in anti-wear protection. This development results, first, for safety reasons (if any contamination occurs at all given potential accidents, this should only be a local contamination) and, second, from method-conditioned simplifications. In the latter instance, layers should also be capable of being produced from compounds by simple, thermal decomposition of an initial substance. A typical example is the employment of TEOS (tetra ethyl ortho silicate) for the deposition of $SiO_2$ in semiconductor technology. This fluid has a vapor pressure of a few hundred Pa at room temperature. Metallo-organic compounds for metal deposition are usually present in solid form at room temperature. The vapor pressure often lies below 100 Pa. Their reliable and time-constant dosing is an indispensable prerequisite for the reproducible deposition of layers.

Commercially available apparatus that are referred to as "mass flow controller" or "mass flow meter" are usually employed now for designational dosing of gaseous substances. These devices measure the mass flow of the gaseous substance via the thermal conductivity.

Such apparatus work on the principle that a pressure drop is produced in a line for the gaseous substance to be investigated, for example, by diaphragms or laminar elements. Dependent on the pressure difference, a part of the gaseous substance can flow via a bypass capillary arranged parallel thereto. Heating wires that typically heat the gaseous substance to 70° through 100° C. are attached to this capillary. Thermal elements that measure the temperature distribution are also thereby provided.

When no gas flows through the line, then a pressure drop does not arise in the system and, thus, a flow does not arise in the capillary. A uniform, symmetrical temperature distribution therefore derives. The deviation from this distribution that derives given a flow can form the basis for the mass flow as a quantity. Apparatus of the abovementioned type as well as their function are described, for example, in a company brochure "V-MAX The ultimate vapor source" of Tylan GmbH in Eching/Munich.

One problem given such apparatus is that an admission pressure of at least $10^3$ through $10^4$ Pa is required for the measuring principle in order to produce the pressure drop in the measuring system. This minimally required admission pressure can only be produced at higher temperatures of, for example, more than 100° C. given many substances or materials, being produced via their vapor pressure. The following disadvantages derive due to the necessity of heating the materials or substances:

In part, the materials are not adequately thermally stable and decompose before the necessary vapor pressure is reached.

Commercially available "mass flow controllers" are normally limited to an operating temperature of 70° C. This temperature can be somewhat higher only in special designs.

Other disadvantages are that the measuring principle loses precision, the useful signal becomes extremely low and the apparatus can at most be operated only at a fixed temperature.

A further limitation in the use of mass flow controllers is that they must be calibrated to a specific material or, to a specific substance since each substance has a different thermal conductivity. This makes universal employment impossible or limits this decisively. Over and above this, the thermal conductivity data are often not known or are only very imprecisely known.

A further possibility of dosing materials having low vapor pressure uses an inert carrier gas. The carrier gas thereby flows through a container and a saturation of the carrier gas according to the partial pressure ratio of the materials occurs in the ideal case.

As a rule, however, an absolute control of the mass flow is thereby not possible, since the actual degree of saturation can fluctuate greatly and, given employment of mass flow controllers, the carrier gas also contributes to the thermal conductivity.

In general, the following measures are currently practiced for dosing materials.

No control of the material flow ensues, this in fact being the simplest solution in terms of technology and equipment but not offering any possibilities of monitoring whatsoever.

The employment of mass flow controllers and mass flow meters represents a simple monitoring possibility that can be employed for low temperatures from 40° through 50° C. When work must thereby be carried out with a carrier gas and at higher temperatures, then this is also unusable for the afore-mentioned reasons.

Given a pressure regulation, the pressure in the evaporator system through which the carrier gas flows is held constant with pressure sensors and control valves. One thereby proceeds on the basis of an unaltering saturation of the carrier gas with the substance to be doped according to the vapor pressure ratio. One disadvantage, however, is that, first, the vapor pressure curve of the material must be exactly known—this usually not being the case and, second, one must proceed on the basis of ideal conditions—among other things, a long dwell time of the carrier gas in the evaporator.

In summary, all previously known possibilities are not satisfactory, particularly in the temperature range above 50° C., and that a reliable, absolute statement about the actual mass transport of a material during the course of a process, for instance in a CVD process, is not possible.

SUMMARY OF THE INVENTION

It is an object of the present invention to improve the determination of the mass flow of materials having, in particular, a low vapor pressure that, in particular, are also suitable for in situ monitoring of the dosing of the materials in deposition processes.

This object is inventively achieved by a method for determining the mass flow of gases on the basis of optical absorption, having the steps of conducting the totality of gases through an absorption cell, storing a reference gas in a reference cell, optically transirradiating said cells, detecting optical radiation emerging from said cells and generating a signal corresponding to a quantity for the mass flow to be identified.

Further, the object is inventively achieved in an apparatus for determining the mass flow of gases on the basis of optical absorption, having an absorption cell, a reference cell having a reference gas contained therein, means for optically transirradiating said cells to generate optical radiation, means for detecting optical radiation emerging from said cells, and means for generating a signal representing a quantity for said mass flow.

BRIEF DESCRIPTION OF THE DRAWINGS

The invention shall be set forth in greater detail below with reference to exemplary embodiments shown in the figures.

DESCRIPTION OF THE PREFERRED EMBODIMENTS

The invention is based on employing a known measurement principle that works on the basis of optical absorption in various wavelength ranges for determining the actual mass flow of a material. It thus becomes possible to make measurement ranges that could previously not be covered employable for the control of the mass flow in a deposition process, particularly given processes having under-pressure. The wavelength range from ultraviolet over the visible range into the remote infrared range corresponding to the composition of the material to be investigated (organic, organometallic, metal halides. . . , etc.) can thereby be exploited. A rough estimate showed that a density of the optically active particles of approximately $10^{14}$ cm$^{-3}$ can still be detected with a system that works broad band. Given an absolute pressure of 100 Pa, this corresponds to a carrier gas saturation of 0.01 per thousand. This unanticipated, high sensitivity also allows the mass transport in the under-pressure range to be measured.

Figure 1:
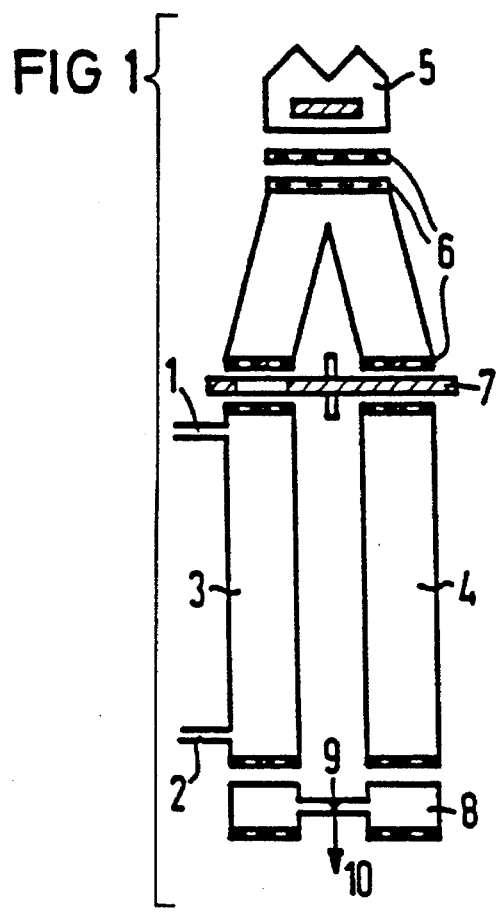
FIG. 1 is a schematic illustration of a known gas analysis apparatus.

FIG. 1 schematically shows the structure of a gas analysis apparatus as described, for example, in a brochure of the assignee bearing the title "Gasanalysegeraete ULTRAMAT 5 OXYMAT 5", No. A19100-E681-A21-V4.

According to the schematic illustration of FIG. 1, such an apparatus has an absorption cell 3 with an admission 1 and an outlet 2 for the material to be investigated. Further, a reference cell 4 is provided that is filled only with a pure, inert gas. Light having a prescribed wavelength range is beamed into the cells 3 and 4 from a light source 5 via an optical filter 6. A rotating chopper 7 is provided between the optical filters 6 and the cells 3 and 4, so that light is alternately beamed into the absorption cell 3 and into the reference cell 4. A detector 8 is optically coupled to the cell system at that side of the cells 3 and 4 facing away from the optical system. Dependent on the concentration of the material to be investigated in the absorption cell 3, different pressure relationships due to differing degrees of heating in the respective detector chambers at the side of the absorption cell 3 and the reference cell 4 derive at a schematically illustrated microflow sensor 9 in the detector 8 which is filled with a gas that absorbs in the same wavelength range as does the substance under investigation. As a result of this pressure difference, gas now flows through a connecting tube wherein the micro-flow sensor 9 is located, flowing from one detector chamber into the other, whereby the micro-flow sensor 9 supplies a signal which represents a quantity for the mass flow of the substance under investigation in the absorption cell 3. This signal is available at a schematically illustrated output 10.

As proceeds from the afore-mentioned brochure, the known gas analysis apparatus is suitable for the quantitative analysis of oxygen concentrations and of various, infrared-absorbent compounds. It has never been utilized in the under-pressure range. The overall structural format of the apparatus (quartz window, cells, etc.) is directed thereto that only a small part of the material under investigation is always conducted into the absorption cell 3. A mass flow could at most be computationally and, thus, imprecisely acquired.

Figure 2:
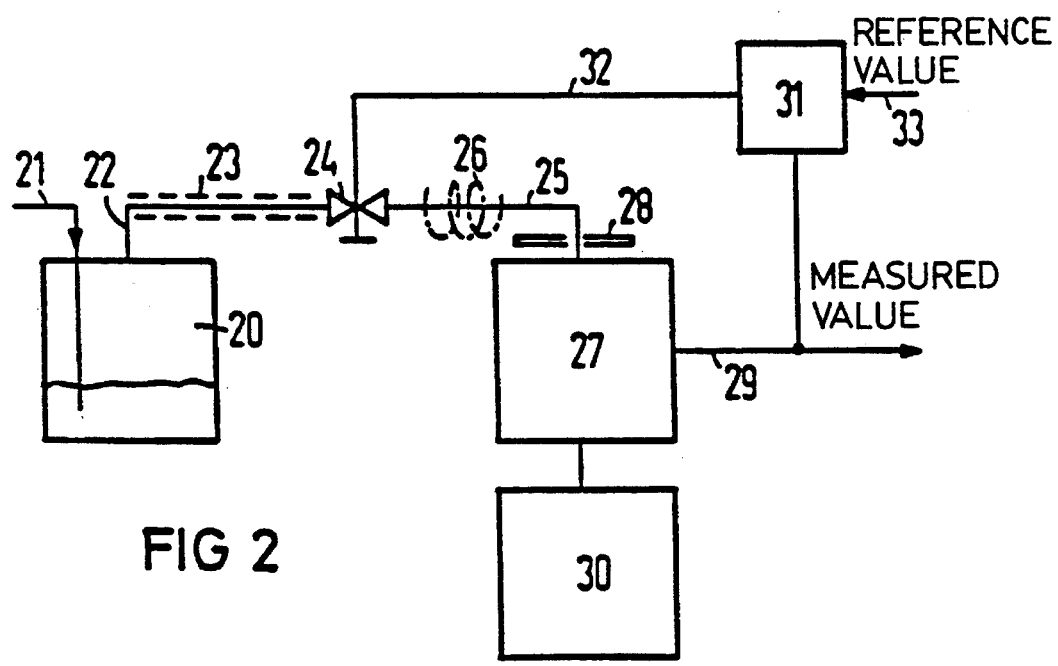
FIG. 2 is a schematic illustration of an employment of the method of the invention for dosing substances given the employment of carrier gas.

By comparison thereto, it is inventively provided to conduct the totality of the material to be dosed via an absorption cell. A structurally adapted apparatus of the type schematically shown in FIG. 1 can be employed upon implementation of the method of the invention in, for instance, a coating process in microelectronics as shown in FIG. 2. A container 20 contains the material to be dosed, whereby a carrier gas is introduced into the container 20 via a schematically illustrated line 20. The carrier gas is conducted through the material to be dosed in the container 20 in order to achieve a saturation of the carrier gas with the dopant. The material to be dosed is thereby admitted into an adapted apparatus 27 of the type shown in FIG. 1 with the carrier gas via a line 22, a control valve 24 and a line 25. From this apparatus 27, the exactly dosed material is introduced into a chamber 30 wherein, for example, a CVD process that is not shown in greater detail is carried out.

An actual signal that represents a quantity for the mass flow of the material to be dosed is available at an output 29 of the mass flow identifying means 27. This actual signal, for example, can be forwarded to a display (not shown). Via a regulator 31 that accepts a rated signal at an input 32, however, this actual signal can also be employed for regulating the control valve 24 and, via the latter, can thus be employed for regulating the dosing of the material from the container 20. The regulator 31 thereby forwards a control signal to the control valve 24 via a line 32.

In order to prevent a demixing of carrier gas and the material to be dosed, an appropriate, schematically shown means 28 that, for example, can be employed as a turbulence plate is expediently provided at the admission of the mass flow identification means 27 in accord with the admission 1 of FIG. 1. This is especially expedient given under-pressure applications, since laminar flow conditions can easily arise given low pressures. This a uniform mixing of carrier gas and material to be dosed may not be present in the absorption cell and measuring errors could potentially resulting therefrom.

When a method of the type set forth above is to be operated at higher temperatures of, for example, up to 120° C., then it is expedient to provide a thermal insulating means and/or a heating means between the source of the material to be dosed in the form of the container 20 and the mass flow identification means 27. This is done in order to keep the temperature of the material under investigation constant. Such a thermal insulation means is shown in FIG. 2 in the form of an insulation 23 of the line 22 schematically shown with broken lines as well as in the form of a heating coil 26 schematically shown with dot-dash lines at the line 25.

An advantage of the present invention is that "in situ" measurement and control of the mass flow is possible during the course of a process.

Another advantage is the response time is approximately 1–20 seconds in practice, whereby the information can be acquired in real time and with chronological resolution.

A further advantage of the present invention is that the measurement is independent of the type and of the amount of the carrier gas since inert gases such as, for example, $H_2$, $N_2$, Ar..., are optically inactive, particularly in the infrared range.

Also, the measurement principle can be employed in a broad and variable range of operating temperatures without re-calibration.

Employment is advantageously possible in the pressure range from a vacuum to normal pressure up to over-pressure. An extremely low admission pressure of only a few Pascals is required for the measuring system and only an extremely slight pressure drop ensues within the overall measuring system, so that employment is also possible for materials having an extremely low vapor pressure.

The present invention has the further advantage that measurement and control for various materials are possible without re-calibration in the concentration range from a few ppm up to high-percentage mixtures.

As an example, the following parameters can be recited for a CVD process of TiN from the organometallic compound tetrakis-(dimethylamino)-titanium-Ti(N(CH$_3$)$_2$)$_4$, which is fluid at room temperature and has a vapor pressure of approximately 5 Pa at 50° C.: Absorption bands of the CH$_x$ group: approximately 3.6 μm Line and cell temperature: 5° through 10° C. above the evaporator temperature Broad band absorption: 3.3 through 3.9 μm.

In general, the following can be recited as ranges of all parameters:
pressure: vacuum to normal pressure up to over-pressure: pressure
temperature: room temperature up to 200° C.
carrier gas flow: 0 through 10,000 sccm
wavelength range: 100 through 10,000 nM (UV, visible, IR)
broad concentration measuring range: a few ppm with carrier gas up to high-percentage mixtures.

The method of the present invention is configured such that, on the one hand, it can be utilized for pure detection of the mass flow and, on the other hand, can also be utilized as an actual value sensor whose signal controls a controlled system and thus actively sets the mass flow, as shown in FIG. 2.

The employment of the method working on the basis of light absorption is especially advantageous in the under-pressure range, which had hitherto never been taken into consideration.

The method is so comprehensive that it can be utilized given practically all dosing and detection problems of materials in the vapor phase. Employment is therefore not limited only to microelectronics or to coating technology.

The method can be unproblematically integrated into an overall system control and can also perform completely independent measuring jobs.

Although other modifications and changes may be suggested by those skilled in the art, it is the intention of the inventors to embody within the patent warranted hereon all changes and modifications as reasonably and properly come within the scope of their contribution to the art.

We claim:

1. Method for setting the mass flow of a gas constituent to be dosed, said gas constituent being a part of a gas mixture, comprising the steps of:

conducting the totality of the gas mixture containing the gas constituent to be dosed into a process chamber through a control valve and an absorption cell;

storing a reference gas in a reference cell;

separately optically transirradiating said absorption cell and said reference cell with the same input optical radiation;

detecting output optical radiation emerging respectively from said absorption cell and said reference cell;

generating a signal corresponding to the optical radiation respectively emerging from said cells; and supplying said signal to the control valve to set the mass flow of the gas constituent to be dosed.

2. Method according to claim 1, wherein said method for setting the mass flow ensues with chronological resolution.

3. Method according to claim 1, wherein said method for setting the mass flow ensues in real time.

4. Method according to claim 1, further comprising a step of:

setting an admission pressure of a few Pa for the gas constituent whose mass flow is to be set.

5. Method according to claim 1, wherein said method is implemented in a broad and variable range of operating temperatures without altering the calibration.

6. Method according to claim 1, wherein said method comprises the step of:

employing gases in the under-pressure range.

7. The method according to claim 1 1 having a gas mixture or underpressure gas mixture the method further comprising the step of:

preventing gas demixing in the region of the absorption cell blending said gas mixture in the region of the absorption cell.

8. The method according to claim 1 having gas mixture temperature above room temperature, the method further comprising the step of:

maintaining said temperature of said gas mixture constant from a gas source to said absorption cell.

9. The method of claim 1 wherein said step of generating a signal corresponding to the optical radiation emerging from said cells is further defined by generating a signal dependent on a difference between the optical radiation respectively emerging from said absorption cell and said reference cell.

10. The method of claim 9 wherein said step of detecting output optical radiation emerging respectively from said absorption cell and said reference cell is further defined by providing a detector having a first chamber and a second chamber optically coupled to the said absorption cell and said reference cell respectively, said detector being filled with a gas that absorbs in the same wavelength range as does the gas constituent; and wherein said step of generating a signal dependent on the difference between the optical radiation respectively emerging from said absorption cell and said reference cell is further defined by generating the signal using a sensor constructed and arranged to sense a pressure differential between said first chamber and said second chamber arising due to respectively different heating of said gas in the respective chambers.

11. An apparatus for setting the mass flow of a gas constituent to be dosed in a gas mixture on the basis of optical absorption, the apparatus comprising:

a process chamber having a control valve;

an absorption cell, the totality of the gas mixture being conducted through said control valve and said absorption cell into the process chamber;

a reference cell having a reference gas contained therein;

means for optically transirradiating separately said cells with the same input optical radiation to generate output optical radiation;

means for detecting said output optical radiation emerging from respective ones of said cells;

means for generating a signal corresponding to the optical radiation emerging from said cells; and a regulator means for providing the signal to the control valve to set the mass flow of the gas constituent to be dosed.

12. An apparatus as claimed in claim 11, further comprising means for preventing gas demixing in the region of said absorption cell.

13. Apparatus of claim 12, wherein said means for preventing gas demixing is a turbulence plate.

14. An apparatus as claimed in claim 12, further comprising a thermal insulation means for keeping the temperature of said gas constant.

15. An apparatus as claimed in claim 12, further comprising a heater means for keeping the temperature of said gas constant.

* * * * *